(12) United States Patent
Rollins et al.

(10) Patent No.: US 11,098,967 B2
(45) Date of Patent: Aug. 24, 2021

(54) INTEGRATED FAN DRIVE SYSTEM FOR COOLING TOWER

(71) Applicant: Prime Datum, Inc., Canandaigua, NY (US)

(72) Inventors: Patrick M. Rollins, Canandaigua, NY (US); George Lucas, Hammandsport, NY (US)

(73) Assignee: PRIME DATUM, INC., Canandaigua, NY (US)

( * ) Notice: Subject to any disclaimer, the term of this patent is extended or adjusted under 35 U.S.C. 154(b) by 0 days.

(21) Appl. No.: 16/808,803

(22) Filed: Mar. 4, 2020

(65) Prior Publication Data

US 2020/0200494 A1 Jun. 25, 2020

Related U.S. Application Data

(63) Continuation of application No. 16/055,062, filed on Aug. 4, 2018, now Pat. No. 10,598,448, which is a continuation of application No. 15/218,473, filed on Jul. 25, 2016, now Pat. No. 10,041,749, which is a continuation of application No. 14/067,177, filed on (Continued)

(51) Int. Cl.
| | |
|---|---|
| *F28F 27/00* | (2006.01) |
| *F04D 19/00* | (2006.01) |
| *F04D 27/00* | (2006.01) |
| *F28F 25/10* | (2006.01) |
| *H02P 29/60* | (2016.01) |
| *F04D 29/66* | (2006.01) |
| *H02P 6/34* | (2016.01) |
| *A61B 17/04* | (2006.01) |
| *F04D 25/06* | (2006.01) |

(Continued)

(52) U.S. Cl.
CPC ........ *F28F 27/003* (2013.01); *A61B 17/0485* (2013.01); *F04D 19/00* (2013.01); *F04D 25/06* (2013.01); *F04D 27/004* (2013.01); *F04D 29/668* (2013.01); *F28C 1/00* (2013.01); *F28F 25/10* (2013.01); *H02P 6/34* (2016.02); *H02P 27/06* (2013.01); *H02P 29/60* (2016.02); *F05B 2270/101* (2013.01); *F28F 2250/08* (2013.01); *Y02B 30/70* (2013.01); *Y10S 261/11* (2013.01); *Y10T 29/49245* (2015.01)

(58) Field of Classification Search
None
See application file for complete search history.

(56) References Cited

U.S. PATENT DOCUMENTS 3,773,650 A * 11/1973 Hislop .................. C10G 73/06
208/33
3,923,935 A * 12/1975 Cates .................... F28C 1/14
261/159

(Continued)

*Primary Examiner* — Bentsu Ro
(74) *Attorney, Agent, or Firm* — Richard T. Black; Foster Garvey PC

(57) ABSTRACT

A drive system for driving a fan in a wet cooling tower, wherein the fan has a fan hub and fan blades attached to the fan hub. The drive system has a high-torque, low speed permanent magnet motor having a motor casing, a stator and a rotatable shaft, wherein the rotatable shaft is configured for connection to the fan hub. The drive system includes a variable frequency drive device to generate electrical signals that effect rotation of the rotatable shaft of the motor in order to rotate the fan.

19 Claims, 6 Drawing Sheets

Related U.S. Application Data

Oct. 30, 2013, now Pat. No. 9,398,908, which is a continuation of application No. 13/353,551, filed on Jan. 19, 2012, now Pat. No. 8,598,823, which is a continuation of application No. 12/524,198, filed as application No. PCT/US2008/077338 on Sep. 23, 2008, now Pat. No. 8,111,028.

(60) Provisional application No. 60/978,916, filed on Oct. 10, 2007.

(51) Int. Cl.
*F28C 1/00* (2006.01)
*H02P 27/06* (2006.01)

(56) References Cited

U.S. PATENT DOCUMENTS

| | | | | | |
|---|---|---|---|---|---|
| 4,784,810 | A | * | 11/1988 | Jorzyk et al. | F28C 1/003 261/17 |
| 5,040,377 | A | * | 8/1991 | Braun | F25B 49/027 62/183 |
| 6,257,007 | B1 | * | 7/2001 | Hartman | F25B 49/027 62/183 |
| 6,718,779 | B1 | * | 4/2004 | Henry | F25B 49/027 62/183 |
| 2006/0125124 | A1 | * | 6/2006 | Koplin | F28C 3/08 261/36.1 |

* cited by examiner

INTEGRATED FAN DRIVE SYSTEM FOR COOLING TOWER

CROSS-REFERENCE TO RELATED APPLICATIONS

This application is a continuation application of U.S. application Ser. No. 16/055,062, filed Aug. 4, 2018, which is a continuation application of U.S. application Ser. No. 15/218,473, filed Jul. 25, 2016, which is a continuation application of U.S. application Ser. No. 14/067,177, filed Oct. 30, 2013, now U.S. Pat. No. 9,398,908, which is a continuation application of U.S. application Ser. No. 13/353,551, filed Jan. 19, 2012, now U.S. Pat. No. 8,598,823, which is a continuation application of U.S. application Ser. No. 12/524,198, filed Jul. 23, 2009, now U.S. Pat. No. 8,111,028, which claims priority to international application no. PCT/US2008/77338, filed Sep. 23, 2008, which claims the benefit of U.S. provisional application No. 60/978,916, filed Oct. 10, 2007. The entire disclosures of the aforesaid U.S. application Ser. Nos. 12/524,198, 13/353,551, 14/067,177, 15/218,473 and 16/055,062 are hereby incorporated by reference.

TECHNICAL FIELD

The present invention generally relates to a fan drive system for a wet cooling tower.

BACKGROUND ART

Wet cooling towers are well known in the art and are used in a variety of industries for cooling fluids such as water. The primary use of large, industrial cooling tower systems is to remove the heat absorbed in circulating cooling water systems used in power plants, petroleum refineries, petrochemical and chemical plants, natural gas processing plants and other industrial facilities. The absorbed heat is rejected to the atmosphere by the evaporation of some of the cooling water in mechanical forced-draft or induced draft towers.

Cooling towers are widely used in the petroleum refining industry. Refining of petroleum cannot take place without cooling towers. Refineries process hydrocarbons at high temperatures and pressures. Cooling water is used to control operating temperatures and pressures. The loss of cooling water circulation within a refinery can lead to unstable and dangerous operating conditions requiring an immediate shut down of processing units. Cooling towers have become "mission critical assets" for petroleum refinery production. As demand for high-end products such as automotive and aviation fuel has risen and refining capacity has shrunk, the refineries have incorporated many new processes that extract hydrogen from the lower value by-products and recombined them into the higher value fuels, improving yield. Many of these processes are dependent on cooling to optimize the yield and quality of the product. Over the past decade, many refineries have been adding processes that reform low grade petroleum products into higher grade and more profitable products such as aviation and automotive gasoline. These processes are highly dependent upon the cooling towers to control the process temperatures and pressures that affect the product quality, process yield and safety of the process. In addition, these processes have tapped a great deal of the cooling capacity reserve in the towers leaving some refineries "cooling limited" on hot days and even bottlenecked. With most U.S. refineries operating well above 90% capacity with attractive profit margins, operating the refinery is critical to operating profit and to pay for the process upgrades implemented over the last decade.

Typically, a wet cooling tower system comprises a basin which holds cooling water that is routed through the process coolers and condensers in an industrial facility. The cool water absorbs heat from the hot process streams that need to be cooled or condensed, and the absorbed heat warms the circulating water. The warm circulating water is delivered to the top of the cooling tower and trickles downward over fill material inside the tower. The fill material is configured to provide a maximum contact surface, and maximum contact time, between the water and air. As the water trickles downward over the fill material, it contacts ambient air rising up through the tower either by natural draft or by forced draft using large fans in the tower. Many wet cooling towers comprise a plurality of cells in which the cooling of water takes place in each cell in accordance with the foregoing technique. Cooling towers are described extensively in the treatise entitled "Cooling Tower Fundamentals", second edition, 2006, edited by John C. Hensley, published by SPX Cooling Technologies, Inc.

Many cooling towers in use today utilize large fans, as described in the foregoing discussion, to provide the ambient air. The fans are enclosed within a fan cylinder that is located on the fan deck of the cooling tower. Drive systems are used to drive and rotate the fans. The efficiency and production rate of a cooling tower is heavily dependent upon the efficiency of the fan drive system. The duty cycle required of the fan drive system in a cooling tower environment is extreme due to intense humidity, icing conditions, wind shear forces, corrosive water treatment chemicals, and demanding mechanical drive requirements.

One commonly used prior art drive system is a complex, mechanical fan drive system that is similar to the type used in agriculture applications. This type of prior art fan drive system utilizes a motor that drives a drive train. The drive train is coupled to a gearbox, gear-reducer or speed-reducer which is coupled to and drives the fan. This prior art fan drive system is subject to frequent outages, a less-than-desirable MTBF (Mean Time Between Failure), and requires diligent maintenance, such as regular oil changes, in order to operate effectively. Furthermore, prior art gearboxes typically require a separate gear to reverse the rotational direction. One common type of mechanical drive system used in the prior art gearbox-type fan drive utilizes five rotating shafts, eight bearings, three shaft seals (two at high speed), and four gears (two meshes). This drive train absorbs about 3% of the total power. Although this particular prior art fan drive system may have an attractive initial cost, cooling tower end-users found it necessary to purchase additional components such as composite gearbox shafts and couplings in order to prevent breakage of the fan drive components. Many cooling tower end-users also added other options such as low-oil shutdown, anti-reverse clutches and oil bath heaters. Thus, the life cycle cost of the prior art mechanical fan drive system compared to its initial purchase price is not equitable.

In a multi-cell cooling tower, such as the type commonly used in the petroleum industry, there is a fan and prior art mechanical fan drive system associated with each cell. Thus, if there is a shutdown of the mechanical fan drive system associated with a particular cell, then that cell suffers a "cell outage". A cell outage will result in a decrease in the production of refined petroleum. For example, a "cell outage" lasting for only one day can result in the loss of thousands of refined barrels of petroleum. If numerous cells experience outages lasting more than one day, the production efficiency of the refinery can be significantly degraded. The loss in productivity over a period of time due to the inefficiency of the prior art mechanical fan drive systems can be measured as a percent loss in total tower-cooling potential. As more cell outages occur within a given time frame, the percent loss in total tower-cooling potential will increase. This, in turn, will decrease product output and profitability of the refinery and cause an increase in the cost of the refined product to the end user. It is not uncommon for decreases in the output of petroleum refineries, even if slight, to cause an increase in the price-per-barrel of petroleum and hence, an increase in the cost of gasoline to consumers. The effect of cell outages with respect to the impact of petroleum product prices is described in the report entitled "Refinery Outages: Description and Potential Impact On Petroleum Product Prices", March 2007, U.S. Department of Energy.

Other types of prior art fan drive systems, such as V-belt drive systems, also exhibit many problems with respect to maintenance, MTBF and performance and do not overcome or eliminate the problems associated with the prior art gearbox-type fan drive systems. One attempt to eliminate the problems associated with the prior art gearbox-type fan drive system is the prior art hydraulically driven fan system. Such a system is described in U.S. Pat. No. 4,955,585 entitled "Hydraulically Driven Fan System For Water Cooling Tower".

Other types of prior art fan drive systems, such as V-belt drive systems, also exhibit many problems with respect to maintenance, MTBF and performance and do not overcome or eliminate the problems associated with the prior art gearbox-type fan drive systems. One attempt to eliminate the problems associated with the prior art gearbox-type fan drive system was the prior art hydraulically driven fan systems. Such a system is described in U.S. Pat. No. 4,955,585 entitled "Hydraulically Driven fan System For Water Cooling Tower".

Therefore, in order to prevent supply interruption of the inelastic supply chain of refined petroleum products, the reliability and subsequent performance of cooling towers must be improved and managed as a key asset to refinery production and profit. An efficient and reliable fan drive system is required to maintain a relatively high cooling efficiency and prevent interruptions in production.

DISCLOSURE OF THE INVENTION

Accordingly, it is an object of the present invention to provide a fan drive system that substantially eliminates the aforementioned problems and disadvantages associated with prior art gearbox-type fan drive systems.

Thus, present invention is directed to, in one aspect, a fan drive system comprising a high-torque, low speed, permanent magnet motor having a rotatable shaft, a fan comprising a hub that is directly connected to the rotatable shaft and a plurality of fan blades that are attached to the hub, and a variable frequency drive device in electrical signal communication with the permanent magnet motor to control the rotational speed of the permanent magnet motor. The variable frequency drive device has a variable frequency controller that has an input for receiving AC power and an output for providing electrical signals that control the operational speed of the high-torque, low speed permanent magnet motor. The variable frequency drive device also includes a user interface in electronic data signal communication with the variable frequency controller to allow a user to input motor speed control data.

In a related aspect, the present invention is directed to the combination of a wet cooling tower having a fan deck, a fan cylinder positioned upon the fan deck, and a fan located within the fan cylinder. The fan comprises a hub to which are connected a plurality of fan blades. The combination further includes a high-torque, permanent magnet motor that has a rotatable shaft connected to the hub, and a variable frequency drive device in electrical signal communication with the permanent magnet motor to control the rotational speed of the permanent magnet motor. The variable frequency drive device comprises a variable frequency controller that has an input for receiving AC power and an output for providing electrical signals that control the operational speed of high-torque, permanent magnet motor, and a user interface in electronic data signal communication with the variable frequency controller to allow a user to input data representing desired motor speeds. The combination further comprises a plurality of sensors in electronic data signal communication with the user interface to provide sensor data signals representing vibration and heat at the bearings of the high-torque, permanent magnet motor, heat of the motor stator, and air flow created by rotation of the fan.

Other objects of the present invention, as well as particular features, elements and advantages thereof, will be elucidated in, or be apparent from, the following description and the accompanying drawing figures.

BRIEF DESCRIPTION OF THE DRAWINGS

Understanding of the present invention and the various aspects thereof will be facilitated by reference to the accompanying drawing figures, submitted for the purposes of illustration only and not intended to define the scope of the invention, in which.

BEST MODE FOR CARRYING OUT THE INVENTION

Figure 1:
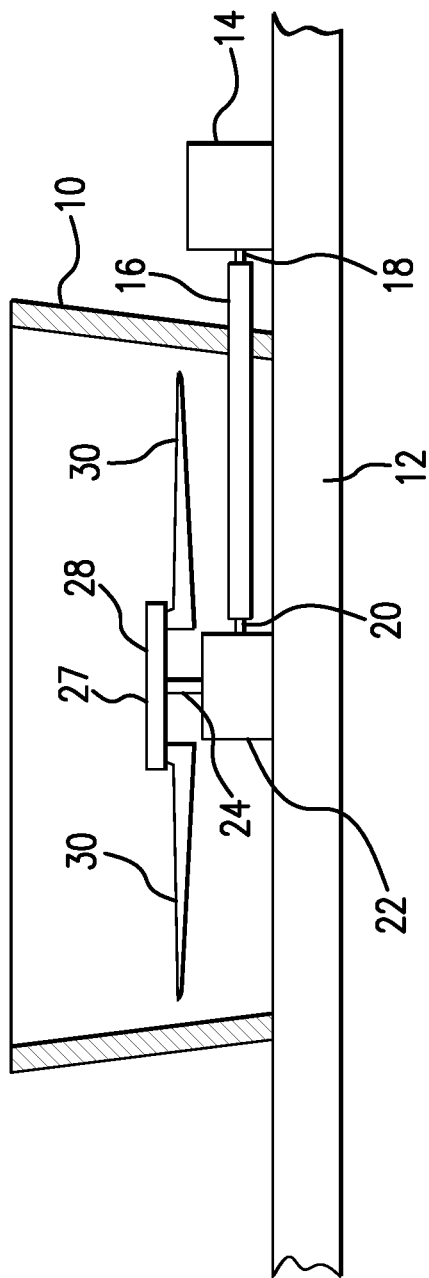
FIG. 1 is an elevational view, partially in cross-section, of a fan cylinder supported by a fan deck of a cooling tower, a fan within the fan cylinder and a prior art gearbox-type fan drive system.

Referring to FIG. 1, there is shown a prior art mechanical fan drive system, and a portion of a wet cooling tower. The remaining portion of the wet cooling tower is not shown since the structure and operation of wet cooling towers is well known in the art. Fan cylinder 10 is positioned on fan deck 12 of the cooling tower. The prior art mechanical fan drive system comprises induction motor 14, drive shaft 16, couplings 18 and 20, and right-angle gearbox 22. Motor 14 is seated on and/or secured to fan deck 12. Gearbox or gear reducer 22 is mounted to or supported by fan deck 12. Gearbox 22 has a vertical shaft 24 that rotates upon rotation of drive shaft 16. As shown in FIG. 1, fan 27 is located within fan cylinder 10 and comprises hub 28 and fan blades 30 that are attached to hub 28. Vertical shaft 24 is connected to fan hub 28. Thus, rotation of vertical shaft 24 causes rotation of fan hub 28 and fan blades 30.

Figure 2A:
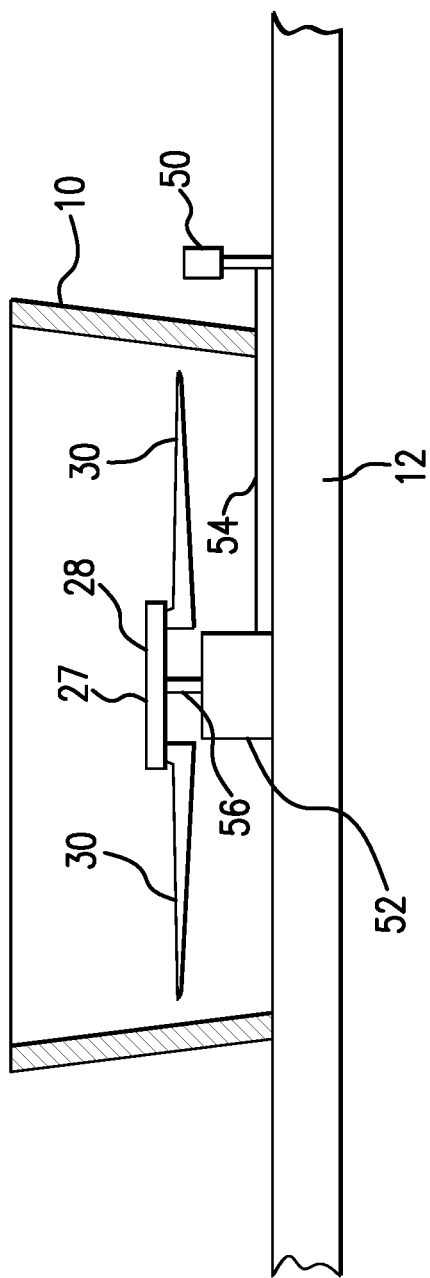
FIG. 2A is an elevational view, partially in cross-section, of a fan cylinder supported by a fan deck of a cooling tower, a fan within the fan cylinder and the fan drive system of the present invention.

Referring to FIG. 2A, there is shown the fan drive system of the present invention. Similar to the view of FIG. 1, a portion of the cooling tower is only shown in FIG. 2A. The fan drive system of the present invention comprises variable frequency drive (VFD) device 50 and motor 52. In accordance with the invention, motor 52 is a high torque, low speed permanent magnet motor. Permanent magnet motor 52 has a high flux density. The superior results, advantages and benefits resulting from permanent magnet motor 52 are discussed in the ensuing description. VFD device 50 and permanent magnet motor 52 are mounted to or supported by fan deck 12. VFD device 50 is in electrical signal communication with permanent magnet motor 52 via cables or wires 54. Permanent magnet motor 52 has shaft 56 that rotates when the appropriate electrical signals are applied to permanent magnet motor 52. Shaft 56 is connected to fan hub 28. Thus, rotation of vertical shaft 56 causes rotation of fan hub 28 and fan blades 30.

Figure 3:
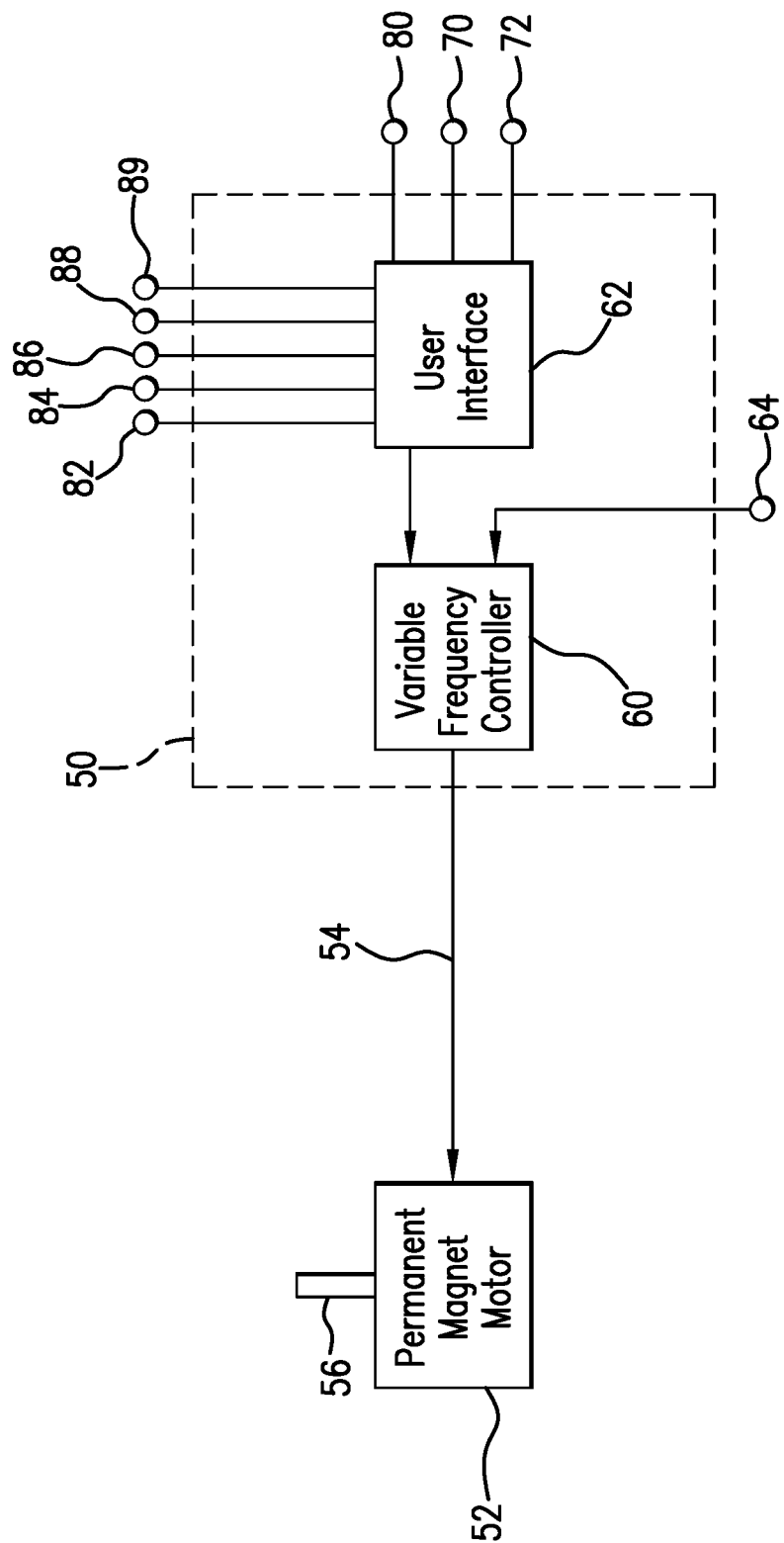
FIG. 3 is a block diagram of the fan drive system of the present invention.

Referring to FIGS. 2A and 3, VFD device 50 comprises a variable frequency controller 60 and a user or operator interface 62. VFD device 50 controls the speed, direction (i.e. clockwise or counterclockwise), and torque of permanent magnet motor 52. AC input power is inputted into variable frequency controller 60 via input 64. Variable frequency controller 60 converts the AC input power to DC intermediate power. Variable frequency controller 60 then converts the DC power into quasi-sinusoidal AC power that is applied to permanent magnet motor 52. User interface 62 provides a means for an operator to start and stop permanent magnet motor 52 and adjust the operating speed of motor 52. In a preferred embodiment, user interface 62 comprises a microprocessor, and an alphanumeric display and/or indication lights and meters to provide information about the operation of motor 52. User interface 62 further includes a keypad and keypad display that allows the user to input desired motor operating speeds. VFD device 50 includes input and output terminals 70 and 72 for connecting push-buttons, switches and other operator interface devices or controls signals. In a preferred embodiment, VFD device 50 further includes a serial data communication port 80 to allow VFD device 50 to be configured, adjusted, monitored and controlled using a computer. In one embodiment, VFD device 50 includes sensor signal inputs 82, 84, 86, 88 and 89 for receiving sensor output signals. The purpose of these sensors is discussed in the ensuing description.

Figure 5:
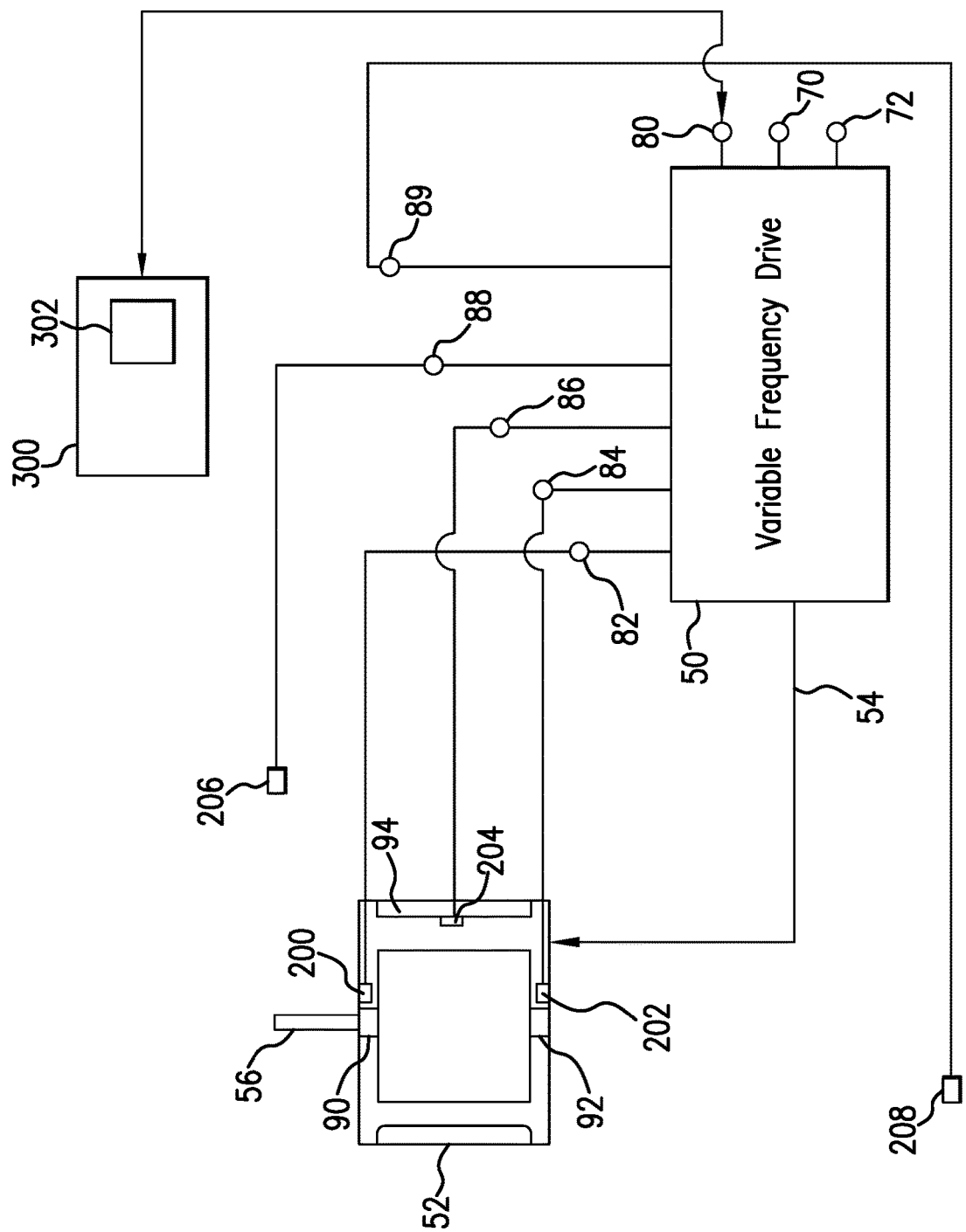
FIG. 5 is a schematic diagram showing the fan drive system of the present invention in conjunction with a plurality of performance monitoring sensors.

Referring to FIGS. 2A and 5, permanent magnet motor 52 is directly coupled to the fan hub 28. Since permanent magnet motor 52 is controlled only by electrical signals provided by VFD device 50, there is no drive shaft, couplings, gear boxes or related components as is found in the prior art gearbox-type fan drive system shown in FIG. 1. In accordance with the invention, permanent magnet motor 52 is a high-torque, low speed motor. Permanent magnet motor 52 is of simplified design and uses only two bearings 90 and 92 (see FIG. 5). Permanent magnet motor 52 includes stator 94. Such a simplified design provides relatively high reliability as well as improved and cost-effective motor production. Permanent magnet motor 52 has relatively low maintenance with a three year lube interval. Permanent magnet motor 52 can be configured with sealed bearings. Permanent magnet motor 52 meets or exceeds the efficiency of Premium Efficiency Induction Motors. Permanent magnet motor 52 substantially reduces the man-hours associated with service and maintenance that would normally be required with a prior art, induction motor fan drive system. In some instances, permanent magnet motor 52 can eliminate up to 1000 man-hours of maintenance and service. Such reliability reduces the amount of cell outages and significantly improves product output. In one embodiment, permanent magnet motor 52 has the following operational and performance characteristics:

Speed Range: 0-250 RPM
Maximum Power: 133 HP/100 KW
Number of Poles: 16
Motor Service Factor: 1:1
Rated Current: 62 A (rms)
Peak Current: 95 A
Rated Voltage: 600 V
Drive Inputs: 460 V, 3 phase, 60 Hz, 95 A (rms max. continuous)

Figure 2B:
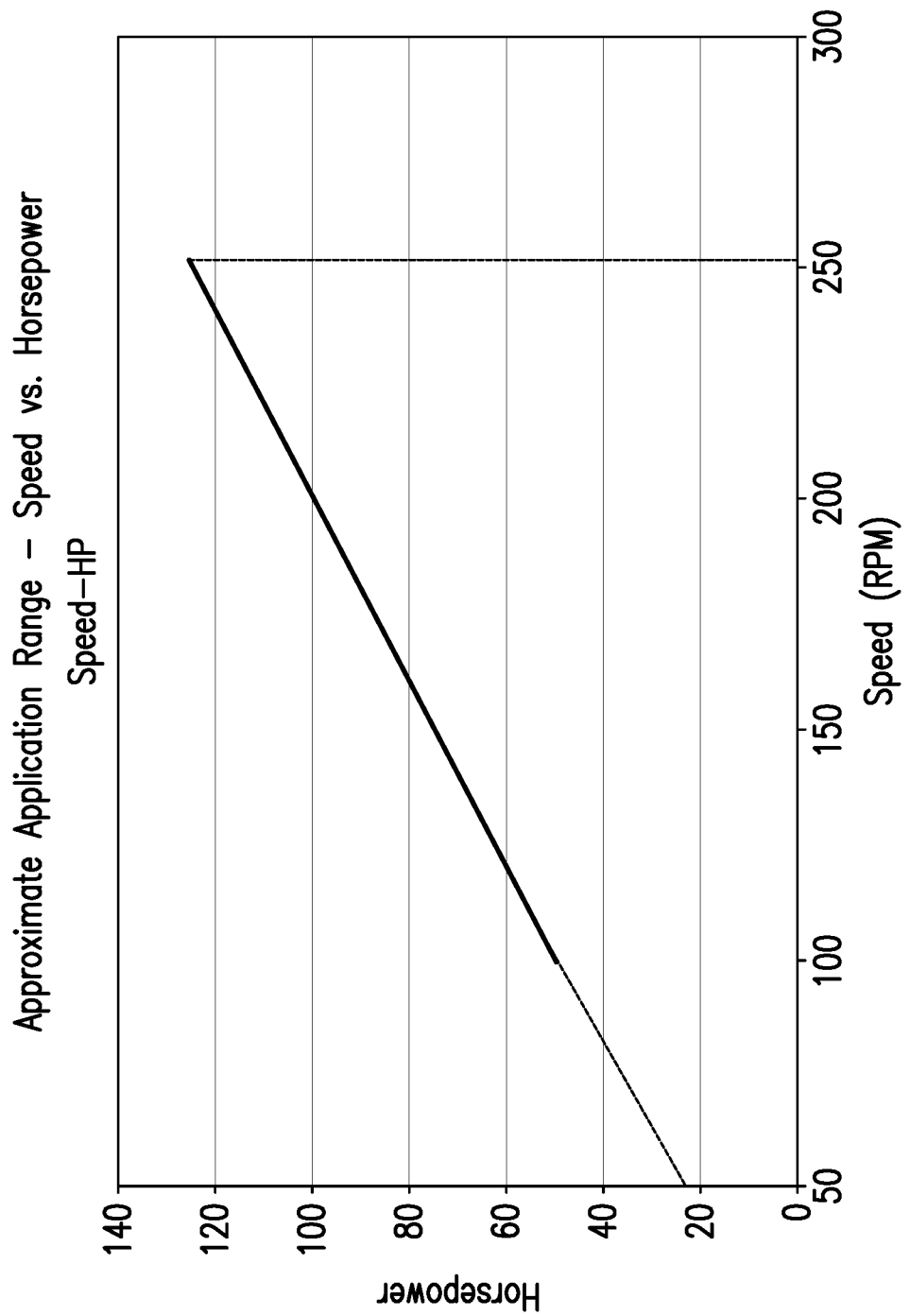
FIG. 2B is a plot of motor speed versus horsepower for a high torque, low speed permanent magnet motor used in one embodiment of the fan drive system of the present invention.

FIG. 2B shows a plot of speed vs. horsepower for high torque, low speed permanent magnet motor 52. However, it is to be understood that the aforesaid operational and performance characteristics just pertain to one embodiment of permanent magnet motor 52 and that motor 52 may be modified to provide other operational and performance characteristics that are suited to a particular application.

Figure 4:
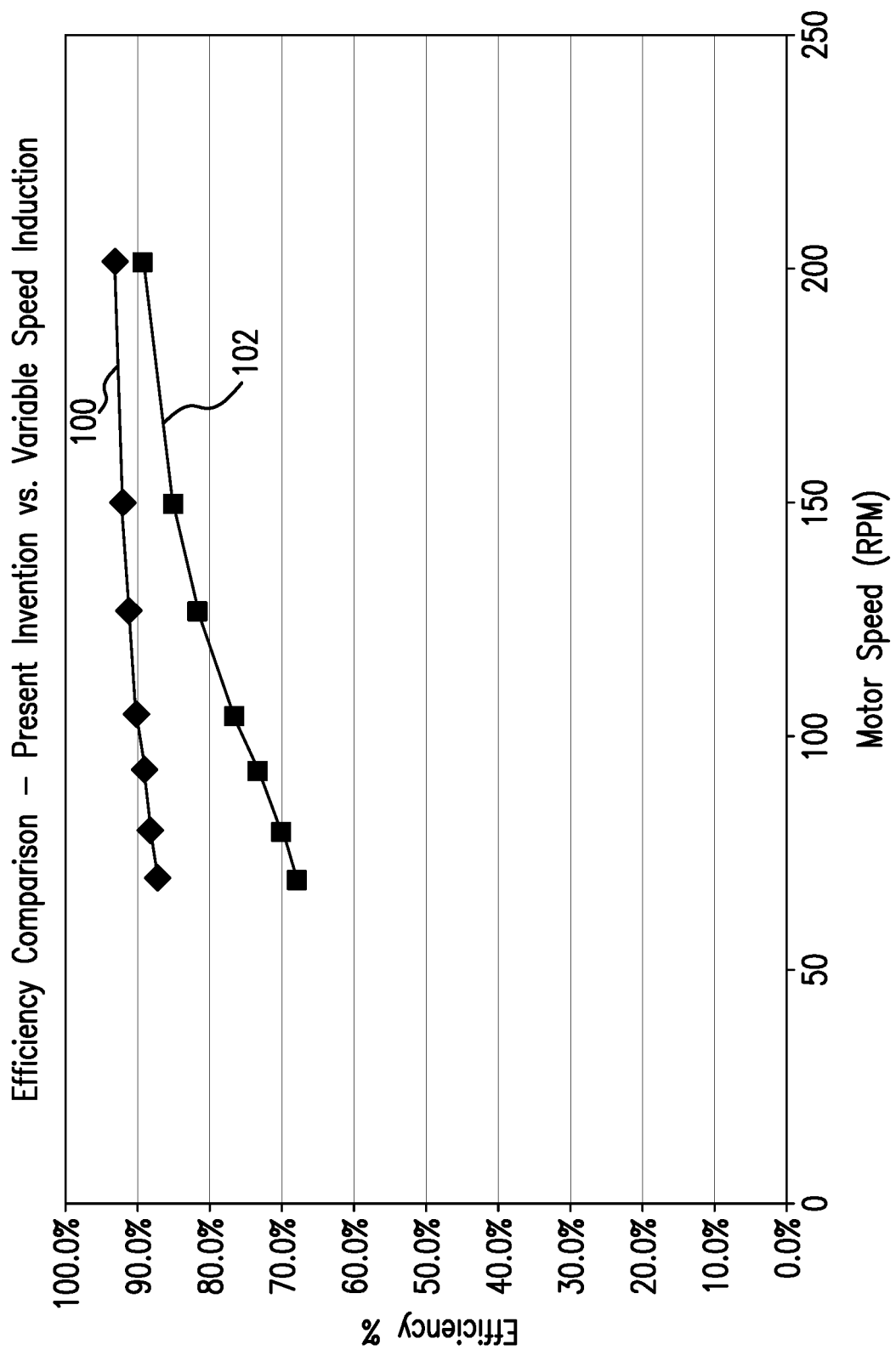
FIG. 4 is a graph illustrating a comparison in performance between the fan drive system of the present invention and a prior art gearbox-type fan drive system that uses a variable speed induction motor.

Referring to FIG. 4, there is shown a graph that shows "Efficiency %" versus "Motor Speed (RPM)" for the fan drive system of the present invention and a prior art fan drive system using a variable speed, induction motor. Curve 100 pertains to the present invention and curve 102 pertains to the aforementioned prior art fan drive system. As can be seen in the graph, the efficiency of the present invention is relatively higher than the prior art fan drive system for motor speeds between about 60 RPM and about 200 RPM.

Referring to FIG. 5, in a preferred embodiment, the fan drive system of the present invention further comprises a plurality of sensors 200, 202, 204, 206 and 208 that provide sensor signals to sensor signal inputs 82, 84, 86, 88 and 89, respectively, of VFD device 50. Sensors 200 and 202 are positioned in proximity to bearings 90 and 92, respectively, of permanent magnet motor 52 in order to sense vibration and heat. Sensor 204 is positioned on stator 94 of permanent magnet motor 52 to monitor heat at stator 94. Sensor 206 is positioned down stream of the air flow created by fan 27 to measure airflow. For purposes of simplifying FIG. 5, fan 27 is not shown. Sensor 208 is located within the basin (not shown) of the wet cooling tower to sense the temperature of the water within the basin. All sensor output signals applied to sensor signal inputs 82, 84, 86, 88 and 89 are inputted into user interface 62 of VFD device 50 and are then routed to an external processing device, such as computer 300, via data port 80. Computer 300 includes a display screen device 302 that enables a user or operator to visually monitor the data outputted by sensors 200, 202, 204, 206 and 208. Computer 300 further includes a user interface, e.g. keyboard, (not shown) that allows an operator to input commands. Computer 300 is configured to implement a reliability algorithm using the data outputted by sensors 200, 202, 204, 206 and 208 and in response, output appropriate control signals that are inputted into user interface 62 via data port 80. Such control signals can be used to adjust the speed of motor 52. Thus, the sensors and computer 300 provide a feedback loop that:

a) monitors vibrations and heat at the bearings of motor 52;

b) monitors heat at the stator of motor 52;
c) monitors airflow produced by fan 27;
d) monitors the temperature of the water in the cooling tower basin;
e) provides a trim balance to compensate for fan-unbalance inertia on the cooling tower structure (i.e. "Hula Effect");
f) alerts the operators to a "blade-out" situation and automatically reduces the speed of motor 52;
g) locks out a particular motor speed that creates resonance;
h) alerts the operator to ice accumulation on fan blades 30 and automatically initiates de-icing operations; and
i) routes the basin-water temperature data to other portions of the industrial process so as to provide real-time cooling feedback information that can be used to make other adjustments in the overall industrial process.

Thus, the fan drive system of the present invention provides many advantages and benefits, including:
a) elimination of many components found in the prior art gearbox-type fan drives, such as drive shafts, couplings, bearings, shaft seals, etc.;
b) elimination of oil changes;
c) significant reduction in service and maintenance;
d) ability to vary the speed of the permanent magnet motor over a relative wide range of speeds;
e) ability to reverse direction of the permanent magnet motor without any additional components;
f) consumption of significantly lower amounts of energy in comparison to prior art gearbox-type fan drive;
g) easy retrofit with existing fan thereby eliminating need to construct new cooling towers;
h) significant reduction in the occurrence of cell outages; and
i) provides significantly more cooling capacity in comparison to prior art gearbox-type fan drive.

The operational logic and system architecture of the present invention will provide the ability to optimize the cooling tower for energy efficiency (e.g. at night when it is cold) and to maximize cooling on hot days or when the process demands additional cooling or to avoid fouling of auxiliary systems such as condenser and heat exchangers.

Although the foregoing discussion is in terms of the applicability of the present invention to the petroleum industry, it is to be understood that the present invention provides benefits to any industry that uses wet cooling towers. Thus, the present invention has applicability to many industries that consume large amounts of energy and are process intensive, such as the power generation, petro-chemical, pulp and paper, chemical, glass, mining, steel and aluminum industries.

It will thus be seen that the objects set forth above, among those elucidated in, or made apparent from, the preceding description, are efficiently attained and, since certain changes may be made in the above construction and/or method without departing from the scope of the invention, it is intended that all matter contained in the above description or shown in the accompanying drawing figures shall be interpreted as illustrative only and not in a limiting sense. It is also to be understood that the following claims are intended to cover all of the generic and specific features of the invention herein described.

What is claimed is:

1. A cooling tower system, comprising:
    a cooling tower structure;
    a variable speed direct-drive system supported by the cooling tower structure, the variable speed direct-drive system comprising a variable speed electric motor having a rotatable shaft, wherein the motor is configured to operate in a forward direction or a reverse direction, the direct-drive system further comprising a programmable motor controller comprising an input for receiving AC power and an output for providing quasi-sinusoidal electrical signals that control one or more of the following: the operational speed (RPM), torque and direction of rotation of the motor, the motor controller being further configured to receive feedback signals to adjust the speed and/or torque and/or direction of rotation of the motor; and
    a fan attached to the rotatable shaft of the motor such that the fan rotates upon rotation of the rotatable shaft.

2. The cooling tower system according to claim 1 wherein the fan includes a fan hub and wherein the rotatable shaft of the motor is connected to the fan hub.

3. The cooling tower system according to claim 1 wherein the motor controller is configured to measure one or more the following: operational speed (RPM) of the motor, electrical current draw of the motor, electrical voltage draw of the motor and/or torque of the motor, the motor controller being further configured to output signals representing the measured operational speed of the motor, the electrical current draw of the motor, the electrical voltage draw of the motor and/or the torque of the motor.

4. The cooling tower system according to claim 3 further comprising a processor to process the signals outputted by the programmable motor controller and generate feedback signals for input into the programmable motor controller.

5. The cooling tower system according to claim 1 further comprising at least one temperature sensing device to sense the temperature and output signals representing the sensed temperature.

6. The cooling tower system according to claim 5 further comprising at least one vibration sensing device to sense vibrations and output signals representing the sensed vibrations.

7. The cooling tower system according to claim 6 further comprising a processor to process the signals representing the sensed temperature and sensed vibration in order to predict impending failures and maintenance.

8. The cooling tower system according to claim 1 further comprising:
    at least one vibration sensing device to sense vibrations and output signals representing the sensed vibrations; and
    a processor configured to process the signals representing the sensed vibrations to determine if such vibrations are the result of resonance produced by one or more motor speeds (RPM).

9. The cooling tower system according to claim 8 wherein the processor is configured to generate feedback signals to the programmable motor controller to control the speed of the motor so as to skip any motor speed (RPM) that that produces an unacceptable vibration.

10. The cooling tower system according to claim 1 further comprising:
    a collection basin for holding cooling water;
    at least one temperature sensor to sense the temperature of the cooling water and output signals representing the sensed temperature; and
    a processor to process the signals representing the sensed temperature and, in response, generate feedback signals for input into the programmable motor controller.

11. The cooling tower system according to claim 1 wherein the motor comprises a permanent magnet motor.

12. The cooling tower system according to claim 1 wherein the programmable motor controller comprises a variable frequency drive.

13. The cooling tower system according to claim 1 further comprising at least one vibration sensing device to sense vibrations and output signals representing the sensed vibrations.

14. The cooling tower system according to claim 13 further comprising a processor to process the signals representing the sensed vibrations and, in response, generate feedback signals for input into the programmable motor controller to control the speed (RPM) of the motor.

15. The cooling tower system according to claim 1 further comprising at least one temperature sensor to sense the temperature and output signals representing the sensed temperature.

16. The cooling tower system according to claim 15 further comprising a processor to process the signals representing the sensed temperature and, in response, generate feedback signals for input into the programmable motor controller.

17. The cooling tower system according to claim 1 wherein the motor is configured with sealed bearings.

18. The cooling tower system according to claim 1 wherein the programmable motor controller is configured to initiate rotation of the fan in accordance with a pre-programmed acceleration rate.

19. The cooling tower system according to claim 1 wherein the programmable motor controller is configured to slow the speed of the fan in accordance with a pre-programmed deceleration rate.

\* \* \* \* \*